United States Patent [19]

Uchiwa et al.

[11] Patent Number: 5,425,937
[45] Date of Patent: Jun. 20, 1995

[54] HAIR TREATMENT COMPOSITION AND HAIR CARE PRODUCT, BOTH CONTAINING ANTI-KERATIN ANTIBODY, AND PRODUCTION OF ANTI-KERATIN ANTIBODY

[75] Inventors: Hideyo Uchiwa; Makoto Hirano, both of Odawara; Umeji Murakami, Kanagawa; Kenichi Sugimoto; Hiromi Minamino, both of Odawara; Toshio Horikoshi, Fujisawa; Minoru Ohta, Miyagi; Takusaburou Ebina, Sendai, all of Japan

[73] Assignee: Kanebo, Ltd., Tokyo, Japan

[21] Appl. No.: 98,398

[22] PCT Filed: Dec. 4, 1991

[86] PCT No.: PCT/JP91/01691

§ 371 Date: Aug. 4, 1993

§ 102(e) Date: Aug. 4, 1993

[51] Int. Cl.$^6$ .................... C07K 16/04; G01N 33/577
[52] U.S. Cl. .............. 424/70.14; 530/388.2; 530/389.3; 530/389.1; 436/547
[58] Field of Search .............. 530/388.25, 388.85, 530/389.1, 389.3, 388.2, 388.7; 435/70.1, 69.7; 424/86, 70; 436/547

[56] References Cited

U.S. PATENT DOCUMENTS 3,128,230 4/1964 Heinbach .............................. 424/86
3,987,161 10/1976 Widder .................................. 424/70

FOREIGN PATENT DOCUMENTS 0127712 12/1984 European Pat. Off. .

OTHER PUBLICATIONS

"Comparison of Stratum Corneum and Hair Fibrous Proteins"; The Journal of Investigative Dermatology, 75:311–315, 1980; vol. 75 No. 4.
"Localization of Low-sulfur Keratin Proteins in the Wool Follicle Using Monoclonal Antibodies"; The Journal of Cell Biology; vol. 102, Apr. 1986, 1412–1418.
"Gamma Globulins of Bovine Lacteal Secretions"; Archives of Biochemistry and Biophysics; vol. 108, 1964, 230–239.
"Characterization of the Serum and Secretory Immune Systems of the Cow and Sheep"; The Journal of Immunology; vol. 103, No. 2 Aug. 1969, 334–344.
"Transfer of Immunoglobulins IgG, IgA and IgM to Lacteal Secretions in the Parturient Sow and Their Absorption by the Neonatal Piglet"; Biochemica et Biophysica Acta 181, 1969 381–392.
"Preparation of Bovine Immunoglobulins and Free Secretory Component and Their Specific Antisera"; Journal of Dairy Science vol. 55, No. 2, 151–164.
"The Nature of the Local Immune System of the Bovine Mammary Gland"; The Journal of Immunology, vol. 118, No. 2, Feb. 1977, 461–465.
"A Procedure for Preparing Immunoglobulin G from Human and Monkey Blood"; Transfusion 6, 146–149, 1966.
"Human Gamma Globulin Fractionation on Anion Exchange Cellulose Columns"; The Journal of Biological Chemistry; vol. 234, No. 10 Oct. 1959, 2645–2651.

(List continued on next page.)

Primary Examiner—David L. Lacey
Assistant Examiner—Susan A. Loring
Attorney, Agent, or Firm—Flynn, Thiel, Boutell & Tanis

[57] ABSTRACT

Hair treatment compositions, hair damage protective agents and hair care products, each contain an active ingredient comprising an antibody which binds to human hair keratins which constitute intermediate-diameter filaments. This antibody can be produced efficiently and in a large quantities from the milk of a bovid animal immunized with said keratins. As this antibody binds to the hair specifically, it is effective in preventing the elution of proteins from the hair, imparting smoothness and flexibility to the hair, and improving the adaptability to combing and luster of the hair.

4 Claims, 3 Drawing Sheets

OTHER PUBLICATIONS

"Immunoglobulin IgA in Bovine Serum and External Secretions"; Biochimica Et Biophysica Acta; 214 (1970) 107–116.

"Substitution of Egg Yolk for Serum in Indirect Fluorescence Assay for Rous Sarcoma Virus Antibody"; Proc. Soc. Exptl. Bio. Med., 126, (1967) 312–315.

"Antibodies to Proteins from Yolk of Immunized Hens"; Immunological Communications, 9(5), (1980), 495–514.

"Immunoperoxidase Anti-Keratin Staining of Epidermal and Pilar Cysts"; British Journal of Dermatology; (1984), III, 63–68.

"The Complement of Native α-keratin Polypeptides of Hair-Forming Cells: A Subject of Eight Polypeptides that Differ From Epithelial Cytokeratins"; Differentiation (1968) 32:101–119.

Virtanen, I. et al., Ann New York Acad. Sci., 455:635–648, 1985.

FIG_1

FIG_2a
Antibody of the invention

FIG_2b
Control antibody

FIG_2c
PBC (Control)

FIG.3A

CBB staining

FIG.3B

Antibody staining

HAIR TREATMENT COMPOSITION AND HAIR CARE PRODUCT, BOTH CONTAINING ANTI-KERATIN ANTIBODY, AND PRODUCTION OF ANTI-KERATIN ANTIBODY

TECHNICAL FIELD

The present invention relates to hair modifiers or hair damage protectives comprising an antibody having an immunological activity to keratins which constitute intermediate filaments which is characteristic of human hair.

The present invention also relates to hair cosmetics, more particularly, hair care products blended with an antibody having an immunological activity to a human hair keratinous protein which constitutes intermediate filaments.

Further, the present invention relates to a process for preparing an anti-hair keratin antibody having an immunological activity to hair keratinous proteins which constitute intermediate filaments, which antibody is useful as the above hair modifiers or hair damage protectives.

BACKGROUND ART

Generally, grooming and cosmetic treatments of hair by washing, brushing, heating with dryers, permanent-waving, hairdyeing or the like, substantially deteriorate and weaken the hair, and destroy the structure of the surface of the hair. Consequently, the hair dries and becomes brittle, split ends are formed or the hair may break, and lose its strength, while hair constituent proteins are eluted by treatments with shampoos, perm chemicals, hair dyes or the like and thus the proteins gradually disappear. Thus, with the elution of the proteins, the hair is made thinner and the likelihood of damage increases. The hair, once damaged, is unable to restore itself to its original state. Therefore, it is necessary to protect the hair from damage and in case of damage, to repair the damaged hair, in order to keep the hair beautiful and healthy.

For this purpose, hydrolysates of various proteins of natural origin or derivatives thereof have been used heretofore as a hair protective ingredient in hair care products such as shampoos, rinses, treating agents and the like. However, these substances have drawbacks such that they are readily washed away with water due to an extremely poor compatibility with hair, particularly because of their high water solubility, so that they have not been sufficiently effective.

On the other hand, U.S. Pat. No. 3,987,161 discloses a method for imparting improved body and set retention to the hair, using an antiserum which is prepared by using hair particles per se as an antigen. However, the antiserum prepared by this method binds to hair proteins so weakly that it has not been satisfactorily effective in preventing the elution of proteins from the hair or repairing the damaged hair.

Incidentally, hair consists of 3 types of cells: an outer cuticle wrapping and protecting the hair fiber, a cortex, i.e. the hair fiber itself, and a central medulla (hair medulla).

Among them, the cortex is composed mainly of three different types of proteins: fibrous "keratins which constitute filaments" (or $\alpha$-keratinous fibrous proteins), non-fibrous "matrix proteins" and cell membrane peripheral proteins.

It has been known that the keratins which constitute intermediate filaments also exist in epidermis, nails, down, etc. are insoluble in water and solubilized in the presence of a denaturing agent, such as urea, SDS or the like, or a reducing agent, or by means of a chemical modification or the like. These proteins which originate from hair contain plenty of cystine and proline but little glycine, while those of an epidermis origin contain plenty of glycine and serine.

In the present invention, keratins which constitute intermediate filaments, which are obtained by solubilizing hair (nails or the like) under severe conditions as described above are employed, other than mere hair particles as described in the aforementioned U.S. Pat. No. 3,987,161.

It is known that an antibody to the keratins which constitute intermediate filaments is produced in the serum of animals such as rabbits, mice, guinea pigs or the like or in a culture solution of spleen cells of such animal origin (Baden: J. Jnvest. Dermatol., 75., 311, 1980; Cotton: Br. J. Dermatol., 3, 63, 1984; T. Tazawa: J. Jpn. Dermatol., 95, 157, 1985; Heid: Differentiation, 32, 101, 1986; etc.). However, it has been shown that these antibodies of mouse or guinea pig origin also react with cytokeratin of epidermal origin to histologically stain tissues of epidermal origin. Thus, it is assumed that the resulting antibodies also react on other epidermal portions such as scalps or the like. With respect to the antibodies of rabbit origin, they are difficult to react with skin but do bind to hair. In the above case, however, the hair is incompletely keratinized, because parts, such as follicles and roots, are soft tissue, and the reactivity of this antibody to completely keratinized hair shafts, to which the present invention is directed, is not discussed. It has been a general idea that antibodies do not bind to keratinized portions, as Tazawa (as referred above) and French et al. (J. Cell. Biol., 102, 1412, 1986) have discussed on monoclonal antibodies.

Further, it has been well demonstrated that a female bovid animal is an effective factory for generating antibodies, and generates a serum containing antibodies to antigens that have been injected into her, and in addition generates milk containing the same antibodies as the serum. However, the reactivity to skin or hair of antibodies manufactured by using, as an antigen, keratins which constitute intermediate filaments has been totally unknown.

DISCLOSURE OF INVENTION

The object of the present invention is to provide hair modifiers which do not bind to skin but bind specifically to hair, form a bond which is not washed off with water or the like, exhibit a damage protective function such as a function of protecting the hair against damage (by preventing elution of proteins, etc.) or repairing the damaged hair, and impart smoothness, suppleness, an improved combability and luster to the hair.

Another object is to provide hair care products which are effective in improving combability, luster and suppleness of the hair, and in repairing or improving the damaged hair.

A further object is to provide a process for mass-producing an anti-hair keratin antibody at a high efficiency.

The present inventors, as a result of assiduous studies for attaining the above objects, have found that an antibody to keratins which constitute intermediate filaments binds specifically to hair so firmly as not to be washed off with water or the like, and is effective in preventing elution of constituent proteins from the hair and repairing damaged hair, and a further useful, prominent effect of improving combability, luster and suppleness of the hair, and eventually have achieved the present invention of hair modifiers or hair damage protectives.

Further, hair care products blended with the hair improver or the hair damage protective have been found also to have a useful, significant effect of improving combability, luster and suppleness of hair, and to be particularly effective for repairing or improving damaged hair, and the present invention has been accomplished.

Alternatively, the inventors have found a process for mass-producing at a high efficiency an anti-hair keratin antibody which binds specifically to hair by virtue of a strong avidity and effectively modifies hair, and accomplished the present invention.

The constitution of the present invention will be explained in detail hereinafter.

As a source of keratins which constitute intermediate filaments (may be referred to simply as "keratin'-'hereinafter) to be used as an antigen in the present invention, mention may be made of human body hair, wool, down, nail or the like. Taking the difference in species into account, the human body hair and the hair of the head are preferred. Particularly, the hair of the head is the most preferable. In order to fractionate keratins from these source materials, any conventional processes may be employed. A generally employable process is used to extract keratins which have been solubilized by cleaving disulfide linkages thereof in the source material through a reducing or oxidizing treatment. In the case of the reducing treatment, the solubilization is effected by preliminarily admixing, as a solubilizing aid, a denaturing agent such as urea, guanidine hydrochloride or the like, under an alkaline condition. Then, the solution from which insoluble matter has been removed by filtration or centrifugation can be an antigen comprising keratins as a main ingredient. More preferably, the antigen is prepared by further conducting dialysis or the like to adequately decrease or remove low-molecular-weight impurities including the denaturing agent. In this instance, aggregation of insolubilized keratins also may be an antigen. Alternatively, iodoacetic acid may be added to the sulfhydryl groups of the above keratins, and then subjected to a carboxymethylation reaction or the like to prepare an antigen comprising aqueous soluble keratins as a main ingredient. More preferably also in this instance, dialysis or the like is additionally conducted to remove low molecular impurities to prepare an antigen. The thus produced antigen may be further subjected to fractionation of keratins by gel filtration, isoelectric precipitation, zincic salt addition or the like, to prepare a purified antigen.

The antibody according to the present invention is obtained by immunizing animals with an antigen, i.e. keratins which constitute intermediate filaments (keratins) contained in human hair, down, nail or the like, or manipulating cell fusion, genetic engineering or the like. The antibody of the invention has an immunological activity to keratins which constitute intermediate filaments of human hair (hereinafter, this antibody is referred to as "anti-hair keratin antibody").

This anti-hair keratin antibody can be obtained by immunizing mammals, birds or the like with the aforementioned antigen according to conventional processes.

An animal to be used for the production of the antibody can be selected appropriately from livestock such as bovid animals, horses, rabbits, fowls or the like. As a bovid animal, all bovines (cows, sheep, goats) which secrete milk are preferred, particularly, cows are most preferred.

Immunization can be effected by a usual method such as Subcutaneous, intraperitoneal, intramuscular, intravenous injection or the like, administration by cannulation or injection into mammary glands or mammary lymph nodes, instillation of nose drops, instillation of eye drops, or the like. Particularly, subcutaneous, intramuscular, intramammary gland or intramammary lymph node or its vicinity administration is more preferred.

The dosage of the antigenic keratins may be appropriately determined to be in such an amount to give a desired antibody titer and not to negatively affect the animals.

If required, the antigen may be used in combination with an adjuvant such as Freund's complete adjuvant (FCA), Freund's incomplete adjuvant (FIA) or the like. Additionally, it may be microencapsulated with a liposome or the like.

The antibody can be isolated from milk, colostrum or serum of these animals, or egg yolk.

The antibody can be isolated from an antibody-producing cell culture according to conventional processes. Namely, splenocytes of mammals or birds immunized with antigenic keratins are fused with a corresponding strain of myeloma to produce hybridomas. One or a plurality of strains of suitable clones are separated from the hybridomas and an antibody can be isolated from supernatant of a culture medium thereof. Alternatively, an antibody or its fragment (a peptide fragment having a property of binding specifically to keratins) can be obtained by introducing and developing a gene of an anti-hair keratin antibody or its fragment in a microorganism such as *Escherichia coli* or the like according to conventional processes, and culturing the microorganism.

Additionally, the titer of the antibody (antibody titer) can be determined by using an enzyme-linked immunosorbent assay (ELISA), radioimmunoassay or the like. If required, changes of the antibody titer, which are traced by the above assay, can be a measure of timing of booster injection or antibody collection.

The anti-hair keratin antibody according to the present invention may be condensed by further extracting, fractionating and isolating immunoglobulin from the above obtained antibody source or a supernatant of antibody-containing culture medium.

Immunoglobulin may be isolated from milk according to any conventional processes. For example, the milk is dialyzed against an acidic buffer solution to separate out impurities comprising casein and lipid as main ingredients which are then removed by centrifugation, and a translucent supernatant is taken out to provide a crude immunoglobulin. Further, if required, an ion-exchange chromatography using an anion exchanger (for example, DEAE-cellulose, DEAE-Sephadex, QAE-Sephadex) is conducted to recover an immunoglobulin fraction. Also if required, a further refinement can be effected either by repeating the same chromatography or by means of gel filtration or affinity [Archives of Biochemistry and Biophysics, 108, 230, (1968); The Journal of Immunology, 103, 334, (1969); Biochimica Et Biophysica Acta, 181, 381, (1969); Journal of Dairy Science, 55, No.2, 151, (1972); and Journal of Immunology, 181, No.2, 461, (1977)].

A number of processes for isolating immunoglobulin from serum or blood plasma of mammals have so far been reported. For example, the processes according to the reports in Transfusion, 6, 146, (1966); Journal of Biological Chemistry, 234, 2645, (1959); Biochemist Biophysica Acta, 214., 107, (1970); etc. are performable.

According to an industrially suitable process, a crude immunoglobulin is obtained from serum or plasma of mammals diluted 2~3 times with saline by means of a stepwise ammonium sulfate precipitation and then, if required, the resultant is further purified by means of fractionation with an ion exchanger, for example, an anion exchanger such as DEAE-cellulose, DEAE-Sephadex or the like, or a cation exchanger such as CM-Cellulose, CM-Sephadex or the like. Further, if required, the fractionation can be conducted by a gel filtration.

A number of processes for isolating immunoglobulin from a vitelline also have so far been reported. For example, the processes according to the reports in Proc. Soc. Exptl. Biol. Med., 126, 312, (1967); Immunol. Commun., 9, 495, (1980); etc. are performable. For example, yolk separated from an egg is diluted with an equal volume of PBS (phosphate buffered saline, pH: 7.4) and further admixed with a double quantity of chloroform to extract and remove lipids. A crude immunoglobulin is obtained from the resulting water layer by precipitation using ammonium sulfate. If required, the resultant is further refined by means of fractionation with an ion exchanger, for example, an anion exchanger such as DEAE-Sepharose, DEAE-Cellulose or the like, or a cation exchanger such as CM-Sepharose, CM-Cellulose or the like. Further, if required, the fractionation can be conducted by means of gel filtration or affinity chromatography.

Further, if required, an enzymatic treatment, such as a treatment with papain or pepsin, or the like, may be conducted to remove an Fc fragment of the immunoglobulin.

In the present invention, it is preferred that the anti-hair keratin antibodies are purified. However, a crude product containing other components may be employable.

The antibodies obtained as above are put to use as an aqueous solution or a dehydrated product produced by a drying procedure such as lyophilization, spray-drying or the like.

The amount of the anti-hair keratin antibody to be blended with hair care products may be appropriately determined in accordance with its dosage according to the form of its application. For example, it may be about 0.00001~80% by weight of an antibody fraction having an antibody titer of at least $10^2$ per 0.1% protein concentration.

The hair modifiers or hair damage protectives according to the present invention contain an anti-hair keratin antibody as an active ingredient.

The hair modifiers or hair damage protectives according to the present invention may be prepared into various compositions formulated according to the form of application to the hair. For example, generally used components can be incorporated in such an amount as not to impair the effects of anti-hair keratin antibodies as hair modifiers or hair damage protectives according to the present invention. As embodiments of the composition, mention may be made of shampoo, rinse, hair conditioner, hair tonic, hair lotion, hair cream, set lotion, hair foam, pomade, hair styling lotion, permanent-waving agent, hairdye, or the like.

The hair care products according to the present invention may be incorporated with a stabilizer, such as a sugar, sugar alcohol, protein, peptide, amino acid, inorganic acid, organic acid or the like, in order to increase the stability of the anti-hair keratin antibody. These stabilizers exhibit an excellent effect on the stabilization of antibody activity according to the present invention. Further, the hair care products according to the present invention may contain a usual ingredient, such as an oily ingredient, surfactant, humectant, alcohol, thickener, antiseptic, UV absorber, colorant, oxidation dye, perfume, refined water, or the like.

BRIEF DESCRIPTION OF THE DRAWINGS

FIG. 2 shows microphotographs of results of indirect immunofluorescent staining. 2(a) A section of a hair shaft reacted with the antibody of the invention. 2(b) A section of a hair shaft reacted with a control antibody obtained from a non-immunized cow. 2(c) A section of a hair shaft reacted with a solvent: PBS.

BEST MODE FOR CARRYING OUT THE INVENTION

The present invention will be further explained in more detail hereinafter by way of example in a non-limiting manner.

The manufacturing examples are for anti-hair keratin antibodies. The antibody titer was determined by using the ELISA method. Namely, a 96-well microtiter plate was coated with 3.9 ng/well of the purified hair keratin antigens. A peroxidase-labeled, goat anti-rabbit-IgG antibody (65-6120, manufactured by ZYMED Laboratories, Inc.) was used as the secondary antibody in the case of measurement of an antibody of rabbit origin, and a peroxidase-labeled, goat anti-bovine-IgG-F(ab')$_2$ antibody (HAF-423, manufactured by E-Y Laboratories, Inc.) in the case of a bovine.

The above was also used as an antibody titer per a 0.1% weight in the case of freeze-dried materials. Further, an IgG concentration of a sample was determined by using a SRID kit (manufactured by The Binding Site Ltd.) and an antibody titer at a 0.1% concentration represented a specific activity. Alternatively, the test examples were evaluated by general test methods of function for hair, i.e., hair protein elution tests, damaged hair restoration tests and performance assessment tests as a functional aspect. The percentages and parts used in the examples are by weight.

MANUFACTURING EXAMPLE 1

Preparation of Antigen 500 mg of hair of a 30 year old man was rinsed with a 2% polyoxyethylene sodium laurylsulfate (3 E.O.) aqueous solution and then suspended in 125 ml of a 0.2M Tris-hydrochloric acid buffer (pH 9.2) containing 6M urea and 0.2M 2-mercaptoethanol. The mixture was stirred for 1 hour at 50° C. and then ground with a TEFLON ® homogenizer. The above extraction procedure was repeated. After centrifugation at 20,000×g for 25 minutes, 120 ml of supernatant was obtained as a keratin fraction. Twenty-four milliliters of the supernatant were dialyzed against a 20 mM Trishydrocholoric acid buffer (pH 9.2) containing 0.85% sodium chloride and 10 mM 2-mercaptoethanol to remove low-molecular-weight impurities, and a keratin antigen (hereinafter referred to as "Antigen A") solution was obtained (65 mg as proteins).

Ninety-six milliliters of the remaining solution containing keratins were admixed with 12 g iodoacetic acid (adjusted to pH 8 with NaOH) and allowed to react for 1.5 hours at room temperature under light-shielding while stirring. The resultant was dialyzed against saline to remove low-molecular-weight impurities, and an aqueous soluble keratin antigen (hereinafter referred to as "Antigen B") was obtained (270 mg as proteins). Four parts of the Antigen B solution (170 mg as proteins) were further admixed with 1 part of a 0.5M sodium acetate buffer (pH 4.2) (pH was adjusted to 4.2 with acetic acid). The mixture was stirred for 1 hour at room temperature to isoelectrically precipitate keratins. It was then centrifuged at 10,000×g for 15 minutes to remove the supernatant and the precipitates were collected. The precipitates were dissolved in a phosphate buffer saline (hereinafter referred to as "PBS") and a purified keratin antigen (hereinafter referred to as "Antigen C") was obtained (134 mg as proteins).

Immunization of Rabbits

Then, the protein concentration of each antigen solution (Antigen A, B or C) was adjusted to 2 mg/ml with PBS and this solution was mixed with FCA at a volume ratio of 1:1 to prepare a water in oil (hereinafter referred to as "W/O") emulsion. A dose of 2 ml/head of this emulsion was subcutaneously administered to 3 rabbits at their several dorsal positions and the same dose was further subcutaneously administered after 2 weeks and 4 weeks. At the sixth week, the same dose of the above antigen solution was further administered into the auricle vein gently and slowly, taking 30 minutes.

Isolation of Antiserum

After a period of one week from the final administration (on the seventh week), the blood was collected from the test animals and centrifuged to isolate an antiserum (hereinafter referred to as "Antiserum A, B or C").

Purification of Antibody

Then, 60 ml each of the obtained antisera was admixed with 60 ml of PBS and further admixed gradually with 80 ml of a saturated ammonium sulfate solution (pH 7.0), and then incubated on ice while stirring for an hour. After centrifugation (10,000×g, 10 min.), the precipitates were collected and dissolved in 60 ml of PBS. Then the above-described ammonium sulfate precipitation was repeated. The obtained precipitates were dissolved in about 120 ml of PBS and dialyzed against PBS diluted to 1/100 concentration. The resulting precipitates were removed by centrifugation and the supernatant was subjected to a lyophilization. Thus, an anti-hair keratin antibody (hereinafter, referred to as "Antibody A, B or C") was obtained. The antibody titer was determined by using the ELISA method. The results are shown in Table 1.

TABLE 1

| Serum | Manufacturing Example 1 | | | Manufacturing Example Antiserum D |
|---|---|---|---|---|
| | Antiserum A | Antiserum B | Antiserum C | |
| Weight of lyophilized product | 610 mg | 750 mg | 510 mg | 540 mg |
| Weight of immunoglobulin | 470 mg | 640 mg | 430 mg | 440 mg |
| Antibody titer of 0.1% conc. | $12 \times 10^3$ | $25 \times 10^3$ | $28 \times 10^3$ | $\leq 1 \times 10^3$ |
| Denotation | Antibody A | Antibody B | Antibody C | Antibody D |

MANUFACTURING EXAMPLE 2

REFERENTIAL EXAMPLE

Preparation of Antigen

Normal human hair was rinsed with a 2% polyoxyethylene sodium laurylsulfate (3 E.O.) aqueous solution and then air-dried. The dried hair was cut into particles with an electric razor to form a powder having a particle size of at most 150 μm.

Immunization of Rabbits

Then, the hair powder was suspended at a concentration of 50 mg/ml in saline and the suspension was mixed with an equal amount of FCA to prepare a W/O emulsion. A dose of 4 ml/head of the obtained emulsion was administered to 3 rabbits by intramuscular injection at two positions of their rump and the same dose was further administered by intramuscular injection after 1 week and 2 weeks.

Isolation of Antiserum

After an elapse of two weeks from the final administration, the blood was collected from the test animals and centrifuged to isolate an antiserum (similar to the antiserum to the hair particles, disclosed in U.S. Pat. No. 3,987,161, hereinafter referred to as "Antiserum D"). The Antiserum D was then treated in the same manner as Manufacturing Example 1, and a lyophilized anti-hair particle antibody (hereinafter referred to as "Antibody D") was obtained. The antibody titer of this antibody was determined as at most $1 \times 10^3$ by the ELISA method.

MANUFACTURING EXAMPLE 3

Preparation of Antigen 5 g of normal hair of a man and 5 g of normal hair of a woman were mixed together and rinsed with a 2% polyoxyethylene sodium laurylsulfate (3 E.O.) aqueous solution and then suspended in 2.5 l of a 0.2M Trishydrochloric acid buffer (pH 9.2) containing 8M urea and 0.2M 2-mercaptoethanol. The mixture was stirred by nitrogen gas bubbling for 1 hour at 50° C. and ground with a TEFLON ® homogenizer. The above procedure was repeated. After centrifuging at 10,000×g for 30 minutes to remove insoluble materials, a hair keratin antigen was extracted.

This antigen was admixed with 200 g of iodoacetic acid (dissolved in 760 ml of a solution containing 400 g of Tris) and allowed to react for an hour at room temperature under light-shielding while stirring. After the reaction was stopped by adding 7 ml of 2-mercaptoethanol, the resultant was dialyzed against a sufficient volume of water and filtrated through a 5 μm mesh to remove insoluble materials. Thus, a hair keratin antigen solution was obtained (6 liters). Four parts of this solution were further admixed with 1 part of a 0.5M sodium acetate buffer (pH 4.2) (the pH was adjusted to 4.2 with acetic acid) and hair keratins were isoelectrically precipitated. After centrifugation at 10,000×g for 10 minutes, the supernatant was removed to collect the precipitates. The precipitates were dissolved in saline. The solution was filtrated through a 0.2 μm mesh to sterilize and further condensed with ultrafiltration membranes to provide a purified hair keratin antigen (2.6 g as proteins).

Immunization of Cow

Then, the protein concentration of the hair keratin antigen solution was adjusted to 20 mg/ml with saline and this solution was mixed with FCA at a volume ratio of 1:1 to prepare a W/O emulsion. The obtained emulsion was subcutaneously administered to the necks of 2 pregnant Horstein-Friesians 2 months before parturition (a 1 ml dose for the cow No.1: an antigen dose of 10 mg/head; a 5 ml dose for the cow No.2: an antigen dose of 50 mg/head). Thereafter, emulsions prepared with FIA, each containing the same amount of the antigen as before, were administered by subcutaneous or intramuscular injection with an interval of 10 days to immunize (the first to the third administration: subcutaneous injection; the fourth to fifth administration: intramuscular injection).

Isolation of Antibody

Colostrum was collected for 3 days from immediately after parturition. The fatty layer was removed by a cream separator and an antibody (hereinafter referred to as "Antibody E-1") was obtained. With this antibody, the skim milk of this experiment was analyzed. The results are shown in Table 2. As is seen from Table 2, even the cows treated with different doses of an antigen were able to produce a sufficient quantity of antibodies.

Purification of Antibody

Further, the milk of these two cows was skimmed and mixed together and subjected to fractionation. 0.1N hydrochloric acid was added to the skim milk to adjust the pH to 4.5 to precipitate casein. The precipitates were roughly removed with a filter cloth and the supernatant was obtained through a continuous centrifugation at 2,500×g. After neutralization, ammonium sulfate was added to the supernatant until a 33% saturation was reached to precipitate an antibody. The precipitates were collected through a continuous centrifugation at 2,500×g and dissolved in PBS. The above ammonium sulfate precipitation procedure was repeated. The resultant was dialyzed against a 10 mM phosphate buffer (pH 7.5) and divided into five aliquots, each applied to a 2-liter DEAE-Cellulose column equilibrated with the same buffer. Then, with the same buffer containing 50 mM sodium chloride, an antibody was eluted and collected (200 g as an antibody). Twenty grams of proteins of this antibody fraction were condensed by ammonium sulfate precipitation and divided into five aliquots, each applied to a Sephacryl S-300 column (5×90 cm) equilibrated with PBS and the main peaks were collected to provide a purified antibody (hereinafter referred to as "Antibody E-2") (15 g as an antibody). It was confirmed as a single band by using SDS-polyacrylamide electrophoretic analysis. Further, the remaining DEAE cellulose purified antibody fraction was divided into 3 aliquots and applied to a column packed with resin conjugated with a purified hair-keratin (Affigel-15; 400 cc). Eluents by a 0.2M glycine-hydrochloric acid buffer (pH: 2.5) were collected and a high purity antibody consisting of a specific antibody (hereinafter referred to as "Antibody E-3") was obtained (3.2 g).

The above-obtained purified antibody and high purity antibody were used in the test examples and application examples described hereinafter. Additionally, a purified antibody was also produced from colostrum of a non-immunized cow by the same procedure as the above and used as a control antibody in the hereinafter described test examples.

MANUFACTURING EXAMPLE 4

Immunization of Cows

The protein concentration of the purified hair keratin antigen solution obtained in Manufacturing Example 3 was adjusted to 20 mg/ml with saline and this solution was mixed with FCA at a volume ratio of 1:1 to prepare a W/O emulsion. A 5 ml dose of the obtained emulsion was administered by intramuscular injection to each of 2 pregnant Horstein-Friesians 2 months before parturition. Two weeks thereafter, an emulsion prepared with FIA, containing the same amount of the antigen as the above was administered by cannulation into the mammary glands.

Isolation and Purification of Antibody

Colostrum was collected for 4 days from immediately after parturition. The fatty layer was removed by a cream separator to provide a skim milk from which an antibody was obtained (hereinafter referred to as "Antibody F"). Further, a purified antibody and a high purity antibody were obtained according to the same purification procedure as Manufacturing Example 3.

The skim milk of this experiment was analyzed and the results are shown in Table 2. As is seen from Table 2, even the cows immunized by intramammary gland administration were able to produce a sufficient quantity of the antibody.

MANUFACTURING EXAMPLE 5

Immunization of Cows

The protein concentration of the purified hair-keratin antigen solution obtained in Manufacturing Example 3 was adjusted to 20 mg/ml with saline and this solution was mixed with FCA at a volume ratio of 1:1 to prepare a W/O emulsion. A 5 ml dose of the obtained emulsion was administered by intramuscular injection to each of 2 pregnant Horstein-Friesians 2 months before parturition. Four weeks thereafter, an emulsion prepared with FIA, containing the same amount of the antigen as the above was administered by injection in the vicinity of the mammary lymph nodes.

Isolation and Purification of Antibody

Colostrum was collected for 4 days from immediately after parturition. The fatty layer was removed by a cream separator to provide a skim milk from which an antibody was obtained (hereinafter referred to as "Antibody G"). Further, a purified antibody and a high purity antibody were obtained according to the same purification procedure as Manufacturing Example 3.

The skim milk of this experiment was analyzed and the results are shown in Table 2. As is seen from Table 2, even the cows immunized by injection administration in the vicinity of the mammary lymph nodes were able to produce a sufficient quantity of the antibody.

MANUFACTURING EXAMPLE 6

The cow once immunized in Manufacturing Example 3 was boosted by cannulation of an emulsion with FIA (an antigen dose of 50 mg) into the mammary gland 2 months before parturition of the next year. Colostrum was collected for 4 days from immediately after the parturition. The fatty layer was removed by a cream separator to provide a skim milk from which an antibody was obtained (hereinafter referred to as "Antibody H"). Further, a purified antibody and a high purity antibody were obtained according to the same purification process as Manufacturing Example 3.

The skim milk of this experiment was analyzed and the results are shown in Table 2. As is seen from Table 2, the cow once immunized was able to produce a sufficient quantity of the antibody by boosting at an appropriate time.

MANUFACTURING EXAMPLE 7

The cow used in Manufacturing Example 4 was boosted by injection of an emulsion with FIA (an antigen dose of 50 mg) in the vicinity of the mammary lymph nodes 3 days after parturition. Watching the changes of the antibody value in the milk, the milk was collected for a month. The fatty layer was removed by a cream separator to provide a skim milk from which an antibody was obtained (hereinafter referred to as "Antibody I"). Further, a purified antibody and a high purity antibody were obtained according to the same purification procedure as Manufacturing Example 3.

TABLE 2

| Manufacturing Example No. | Cow No. | Collected skim milk (kg) | Analysis of antibody in milk | |
|---|---|---|---|---|
| | | | Quantity of IgG (g) | Specific activity* |
| 3 (Antibody E-1) | 1 | 21.3 | 200 | 1600 |
| | 2 | 12.7 | 260 | 1800 |
| 4 (Antibody F) | 3 | 41.0 | 1130 | 16000 |
| | 4 | 37.7 | 580 | 5600 |
| 5 (Antibody G) | 5 | 43.0 | 1060 | 15000 |
| | 6 | 41.1 | 1460 | 4200 |
| 6 (Antibody H) | 2 | 30.4 | 870 | 7000 |
| 7 (Antibody I) | 3 | 510 | 770 | 12000 |

*Antibody titer/quantity of IgG

Figure 1:
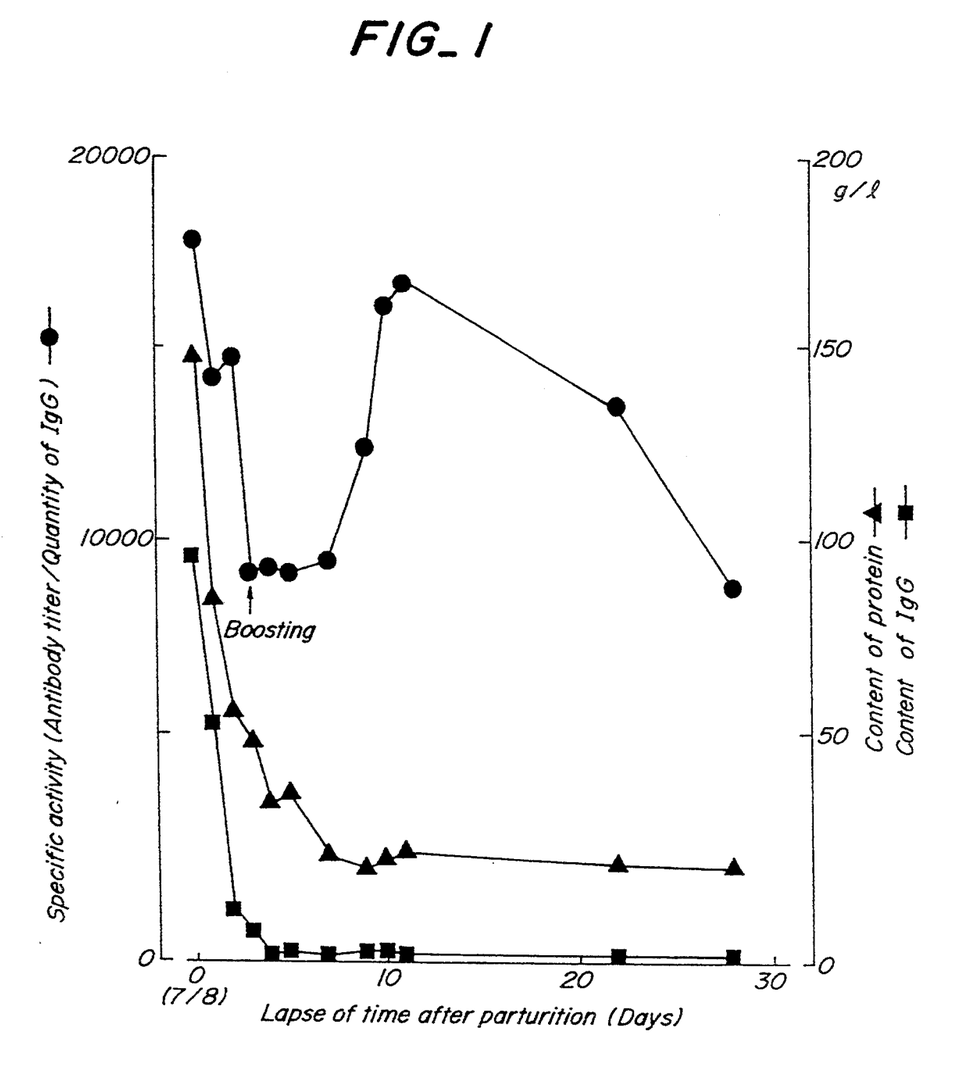
FIG. 1 is a graph showing quantity changes of an antibody in the milk of a cow given a booster with an antigen on the third day after parturition.

The skim milk of this experiment was analyzed and the results are shown in FIG. 1 and Table 2. As is seen from FIG. 1 and Table 2, the cow once immunized was able to produce a sufficient quantity of the antibody from the milk by boosting at an appropriate time.

TEST EXAMPLE 1

Protein Elution Prevention Effect on Hair

A tuft of hair (18 cm, 5 g) was formed by bundling untreated hair of a woman aged 22 which was subjected to 3 repetitive permanent-wave treatments in a usual manner to prepare permanent-wave treated hair. Then, the permanent-wave treated hair was soaked for an hour in 50 ml of PBS containing 1.0% of the Antibody A obtained in Manufacturing Example 1, and washed in water for 10 minutes, followed by being air-dried for 24 hours (hereinafter referred to as "antibody-treated hair").

Then, 0.5 g of the tuft was cut out and put into 10 ml of a 0.07M phosphate buffer (pH: 9.0), followed by being left to stand at 45° C. for 24 hours to allow proteins to elute from the hair. The quantity of the eluted proteins was determined according to the Lowry method. The above procedure was repeated 5 times. The amount of the eluted proteins was determined by the mean value of 5 measurements. The results are shown in Table 3.

Additionally, Table 3 also shows the results of comparative examples conducted in the same manner as the above, except that the permanent-wave treated hair was soaked in PBS not containing an antibody, PBS containing 1.0% of the Antibody D obtained in Manufacturing Example 2, or the collagen hydrolysate (the trademark: PROMOIS W-32R, manufactured by Seiwa Kasei Co., Ltd.), instead of the above PBS containing 1.0% of the Antibody A.

TABLE 3

| Treating conditions | Quantity of proteins eluted from hair (mg/ml) | Tensile strength at break (g/cm$^2$) |
|---|---|---|
| Antibody A | 0.54 | 76.7 |
| Antibody D | 0.61 | 70.4 |
| Collagen hydrolysate | 0.71 | 70.2 |
| PBS (control) | 0.62 | 70.1 |

As is apparent from Table 3, a satisfactory result was obtained in that the anti-hair keratin antibody according to the present invention had an excellent characteristic for preventing elution of proteins from hair. In contrast therewith, in the case where hair tufts were not treated with the anti-hair keratin antibody of the present invention, the anti-hair particle antibody (Antibody D) obtained in Manufacturing Example 2 or the collagen hydrolysate, was not very effective in preventing elution of proteins from the hair.

TEST EXAMPLE 2

Repairing Effect on Damaged Hair

In order to determine the tensile strength of hair as a measure of the repairing effect on damaged hair, 50 hair fibers were taken out of the antibody-treated hair tuft prepared in Test Example 1 and the diameter and tensile strength at break of the hair were determined with a tensile strength tester (manufactured by L.B Chemical, Ltd.). Tensile strengths at break per unit cross-sectional area were calculated and the mean value of 50 hair fibers was determined. The results are shown in Table 3.

Additionally, Table 3 also shows the results of comparative examples conducted in the same manner as the above, except that the hair fibers were soaked in PBS not containing an antibody, PBS containing 1.0% of the Antibody D obtained in Manufacturing Example 2, or a collagen hydrolysate (the trademark: PROMOIS W-32R), instead of the above PBS containing 1.0% of the Antibody A.

As is apparent from Table 3, a satisfactory result was obtained in that the anti-hair keratin antibody according to the present invention had excellent characteristics of recovering deteriorated strength of damaged hair and preventing broken or split hairs. In contrast therewith, the hair strength of the tufts not treated with the anti-hair keratin antibody of the present invention, namely, those treated with the anti-hair particle antibody (Antibody D) obtained in Manufacturing Example 2 or the collagen hydrolysate, did not recover significantly.

TEXT EXAMPLE 3

Hair Modification Effect from Functional Aspects—Combability, Luster, Suppleness and Feel In order to investigate the effect on modification of hair combability, 50 hair fibers were taken out of the antibody-treated hair tuft prepared in Test Example 1 and the kinetic frictional coefficient of the hair fiber was determined by using a Radar-process friction measuring apparatus (manufactured by Nippon Rheology KiKi Inc.), and the mean value of 50 hair fibers was calculated.

Furthermore, in order to investigate another effect on modification of the luster of the hair, 30 hair fibers were removed likewise from the antibody-treated hair tuft prepared in Test Example 1 and the luster was measured by using a goniophotometer (manufactured by Murakami Color Research Laboratory). The luster value was calculated according to the following equation and the mean value of 30 hair fibers was calculated. Luster value=(amount of specularly reflected light—amount of diffusedly reflected light)/(amount of diffusedly reflected light)

Then, 10 inspection specialists conducted a sensory evaluation of suppleness and feel by comparing the above antibody-treated tufts with tufts which were not treated using the antibody. The number of people who decided on each description of the results are shown The results of the evaluation of the above combability, luster, suppleness and feel are shown in Tables 4 and 5.

Additionally, Tables 4 and 5 also show the results of comparative examples conducted in the same manner as above, except that the tuft was soaked in PBS not containing an antibody, PBS containing 1.0% of the Antibody D obtained in Manufacturing Example 2, or a collagen hydrolysate (the trademark: PROMOIS W-32R), instead of the above PBS containing 1.0% of the Antibody A.

TABLE 4

| Treating conditions | Kinetic frictional coefficient | Gloss value of hair |
|---|---|---|
| Antibody A | 0.110 | 20.1 |
| Antibody D | 0.133 | 15.4 |
| Collagen hydrolysate | 0.131 | 15.5 |
| PBS (control) | 0.135 | 15.5 |

TABLE 5

| Treating conditions | Suppleness | | | Feel | | |
|---|---|---|---|---|---|---|
| | Good | Un-changed | Poor | Good | Un-changed | Poor |
| Antibody A | 9 | 1 | 0 | 7 | 2 | 1 |
| Antibody D | 0 | 9 | 1 | 1 | 9 | 0 |
| Collagen hydrolysate | 0 | 8 | 2 | 0 | 7 | 3 |
| PBS (control) | 0 | 7 | 3 | 0 | 7 | 3 |

As is apparent from Tables 4 and 5, prominent results were obtained in that the anti-hair keratin antibody A according to the present invention was excellent, both in combability and luster and could impart a good feel to the hair. Further, the antibodies B and C also exhibited an excellent effect to the same degree. In contrast therewith, the tufts of hair not treated with the anti-hair keratin antibody of the present invention, namely, those treated with Antibody D or the collagen hydrolysate, were not improved.

TEST EXAMPLE 4

Test for Binding to Hair

Binding-of the anti-hair keratin antibody manufactured according to the present invention to hair (the hair shaft) was confirmed by means of an indirect immunofluorescent staining technique. Normal hair of a male human (26 years old) was cut into an appropriate length, soaked in TISSUE TEC II-OCT compound for at least 30 minutes and frozen. A 6 μm thick section was sliced off from the frozen block with a cryostat and applied onto a non-fluorescent slide glass coated with 3% gelatin (manufactured by Difco Laboratories). After being air-dried sufficiently, it was fixed for 20 minutes at room temperature with 4% paraformaldehyde, followed by 3 repetitions of a 10 minute washing with PBS.

On the other hand, the high purity antibody (Antibody E-3) obtained in Manufacturing Example 3 or the immunoglobulin obtained by purifying colostrum of a non-immunized cow (hereinafter referred to as "Control Antibody") was diluted to a concentration of 0.5 mg/ml with PBS containing 10% of rabbit serum (hereinafter referred to as "10% serum PBS") and reacted with the above-described tissue sections at room temperature for 30 minutes.

Figure 2A:
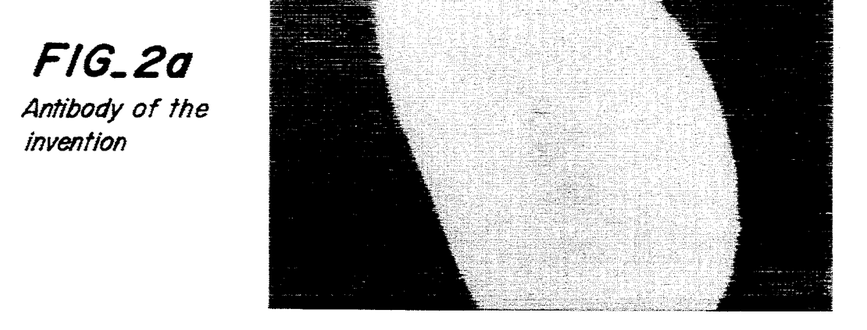
Figure 2B:
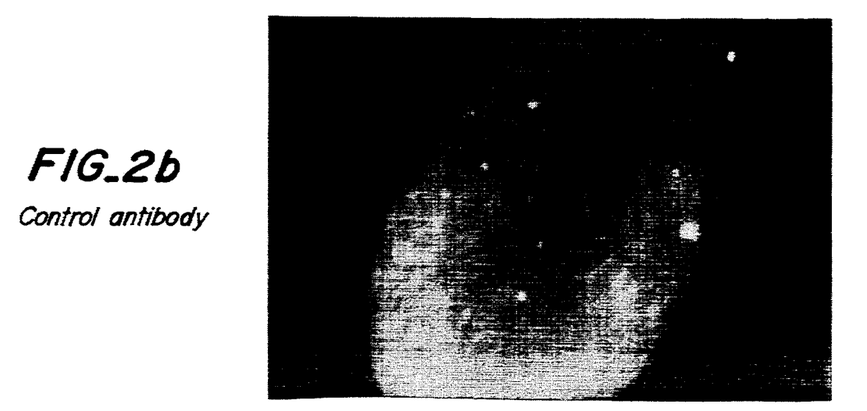
Figure 2C:
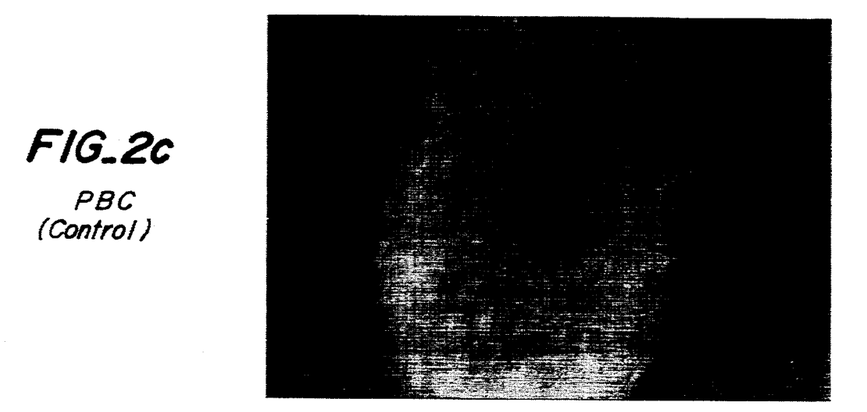

After 3 repetitions of a 10 minute washing with PBS, 10% of a fluorescein isothiocyanate (FITC) labeled rabbit anti-bovine immunoglobulin antibody (which had been diluted with serum PBS) as the secondary antibody was reacted for 30 minutes at room temperature under light-shielding. After 3 repetitions of a 10 minute washing with PBS, it was encapsulated and microscopically examined. The results are shown in FIG. 2.

Fluorescence development was observed over the entire surface area of only the hair shaft of the specimen which was reacted with the anti-hair keratin antibody to demonstrate the binding of the antibody to the hair.

TEST EXAMPLE 5

Test of Reactivity with Skin

In order to examine whether the anti-hair keratin antibody manufactured according to the present invention is specific to hair, the reactivity of the antibody with keratins of trichocytic origin and spidermal origin were tested according to the Western-blotting method.

Fifty ng each of keratin of trichocytic origin (the keratins which constitute intermediate filaments extracted from human hair in Manufacturing Example 3) and a keratin of epidermal origin (K 0253, manufactured by Sigma Chemical Co.) was electrophoresed in an SDS-10% polyacrylamide gel and transferred to a nitrocellulose membrane (manufactured by Nihon Millipore Ltd.) according to the process of Towbin et al.

This membrane was blocked overnight in a Trishydrochloric acid buffered saline (hereinafter referred to as "TBS") containing 3% of gelatin (manufactured by Difco Laboratories) in a refrigerator. After 3 repetitions of a 5 minute washing with TBS containing 0.1% of Tween 20 (hereinafter referred to as "TBST"), the purified antibody obtained in Manufacturing Example 3 (Antibody E-2) the concentration of which was further adjusted into 0.1 mg/ml was reacted therewith at room temperature for an hour.

After 3 repetitions of a 5 minute washing with TBST, a peroxidase-labeled goat anti-bovine IgG·F(ab')$_2$ antibody (HAF-413, manufactured by E-Y Laboratories, Inc.; which had been diluted 1,200 fold with TBST) was reacted therewith at room temperature for an hour.

After 3 repetitions of a 5 minute washing with TBST, the blots were developed using, as a substrate, 0.05% 4-chloro-1-naphthol containing 0.01% of $H_2O_2$.

Additionally, in the case of CBB staining which is shown as a control, the quantity of the electrophoresed protein was 5 μg each. The results are shown in FIG. 3.

Figure 3A:
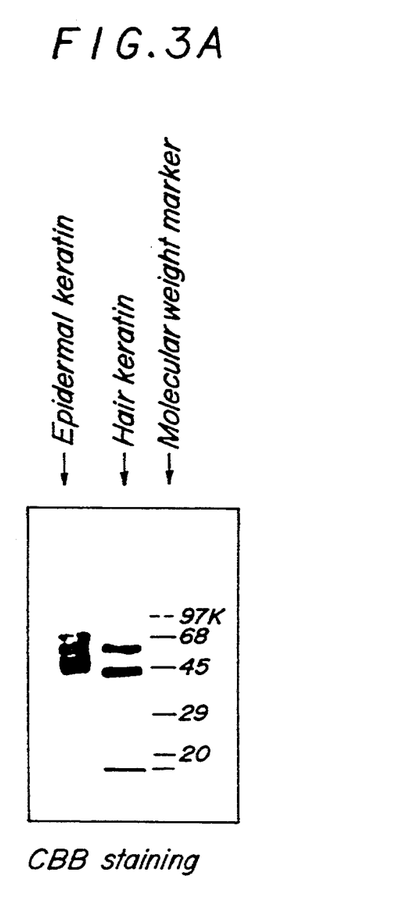
FIG. 3(a) shows a result of a CBB staining of hair keratins and epidermal keratins transferred to a membrane.
Figure 3B:
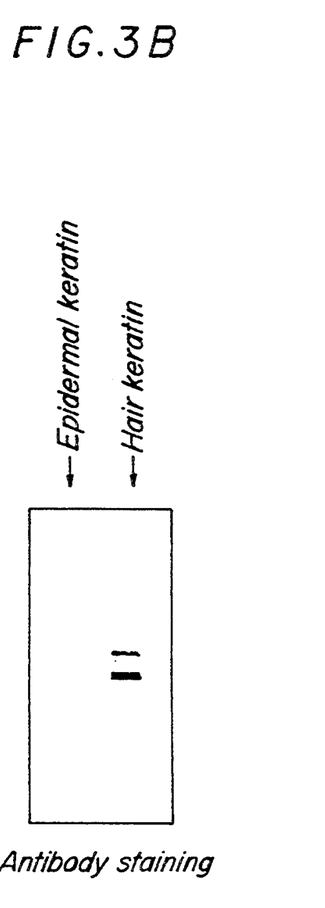
FIG. 3(b) shows a test result of reactivities of similarly treated hair keratins and epidermal keratins with the antibody of the present invention.

From FIG. 3, it can be observed that the anti-hair keratin antibody reacts only with the keratin protein of human trichocytic origin, indicating that the antibody is very weakly reactive to skin.

TEST EXAMPLE 6

Protein Elution Prevention Effect on Hair

A tuft of hair (18 cm, 5 g) was formed by bundling hair of a woman which was subjected to 3 repetitive permanent-wave treatments in a usual manner to prepare a permanent-wave treated hair. Then, the permanent-wave treated hair was soaked for an hour in 50 ml of PBS containing 1.0% of the purified antibody (Antibody E-2) obtained in Manufacturing Example 3, and then washed in water for 10 minutes, followed by being air-dried for 24 hours (hereinafter referred to as "antibody-treated hair").

Then, 0.5 g of the tuft was cut out and put into 10 ml of a 0.07M phosphate buffer (pH: 9.0), followed by being left at 45° C. for 24 hours to allow proteins to elute from the hair. The quantity of the eluted proteins was determined according to the Lowry method. The above procedure was repeated 5 times. The amount of the eluted proteins was determined by the mean value of 5 measurements. Additionally, the results of comparative examples conducted in the same manner as above, except that the permanent-wave treated hair was soaked in PBS not containing an antibody, a PBS solution containing 1% of the control Antibody (refer to Manufacturing Example 3), or PBS solution containing 1% of collagen hydrolysate (the trademark: PROMOIS W-32R), instead of the above PBS containing 1.0% of the above antibody, are shown in Table 6 together with the above results.

TABLE 6

| Treating conditions | Quantity of proteins eluted from hair (mg/ml) |
| --- | --- |
| Antibody E-2 | 0.53 |
| Control antibody | 0.68 |
| Collagen hydrolysate | 0.92 |
| PBS (control) | 0.66 |

As is apparent from Table 6, a good result was obtained in that the anti-hair keratin antibody according to the present invention has an excellent characteristic of preventing elution of proteins from the hair. In contrast therewith, the ordinary antibody having no specificity or the collagen hydrolysate was not very effective in preventing elution of proteins from hair.

TEXT EXAMPLE 7

Repairing Effect on Damaged Hair

In order to determine a tensile strength of hair as a measure of the repairing effect on damaged hair, a tuft of female human hair which was brushed for 10,000 stokes and physically damaged was treated in the same manner as Test Example 3 with PBS containing 0.01–1% of the purified antibody obtained in Manufacturing Example 3 (Antibody E-2). From the tuft 50 hair fibers were taken out and the tensile strength at break of the hair fiber was measured with a tensile strength tester (manufactured by L.B Chemical, Ltd.). The mean value of 50 hair fibers was calculated. As a comparative example, hair fibers treated with PBS and with a 1% control antibody PBS solution were used. The results are shown in Table 7.

TABLE 7

| Treating conditions | | Tensile strength at break (g) |
| --- | --- | --- |
| Antibody E-2 | 1% | 86.7 |
| | 0.1% | 81.0 |
| | 0.01% | 80.3 |
| Control antibody | 1% | 75.4 |
| PBS (control) | | 74.0 |

Further, the effect of the above antibody was compared with commercially available hair modifiers. Tufts were treated with PBS containing 1.0% of the purified antibody obtained in Manufacturing Example 3 (Antibody E-2), the collagen hydrolysate, or the cationized cellulose (the trademark: LEOGUARD, manufactured by LION CORP.) and equally tested. The results are shown in Table 8.

TABLE 8

| Treating conditions | Tensile strength at break (g) |
| --- | --- |
| Antibody E-2 | 81.3 |
| Collagen hydrolysate | 76.0 |
| Cationized cellulose | 73.1 |
| PBS (control) | 74.9 |

As is apparent from Tables 7 and 8, since it binds specifically to the hair, the anti-hair keratin antibody according to the present invention has excellent properties and brings about satisfactory results. For example, the damaged hair is restored to its original strength, and breaking or splitting of the hair is prevented. In contrast therewith, the existing hair modifiers, namely, the collagen hydrolysate and the cationized cellulose were not very effective in restoring the original strength of the hair.

TEST EXAMPLE 8

Effects on Hair Modification from Functional Aspects—Luster, Combability, Suppleness and Feel In order to investigate an effect on modification of luster of hair, permanent-waved female human hair was treated in the same manner as Test Example 3 with PBS containing 1.0% of the purified antibody obtained in Manufacturing Example 3 (Antibody E-2) and the luster value was calculated, and the mean value of 30 hair fibers was determined.

As comparative examples, hair treated with PBS, a 1% control antibody PBS solution or a collagen hydrolysate was employed. The results are shown in Table 9.

TABLE 9

| Treating conditions | Gloss value of hair |
| --- | --- |
| Antibody E-2 | 21.9 |
| Control antibody | 15.3 |

TABLE 9-continued

| Treating conditions | Gloss value of hair |
| --- | --- |
| Collagen hydrolysate | 15.9 |
| PBS (control) | 15.0 |

In order to investigate another effect on the modification of hair combability, a tuft of brushed female human hair was treated in the same manner as Test Example 6 with a 1% solution of the purified antibody obtained in Manufacturing Example 3. From the hair tuft, 50 hair fibers were removed and the kinetic frictional coefficient of the hair was measured by using a Radar-process friction measuring apparatus (manufactured by Nippon Rheology KiKi Inc.). The mean value of 50 hair fibers was calculated.

As comparative examples, tufts each treated with PBS, a 1% control antibody PBS solution or a collagen hydrolysate were employed. The results are shown in Table 10.

TABLE 10

| Treating conditions | Kinetic frictional coefficient |
| --- | --- |
| Antibody E-2 | 0.118 |
| Control antibody | 0.125 |
| Collagen hydrolysate | 0.124 |
| PBS (control) | 0.126 |

Then, 10 inspection specialists conducted a sensory evaluation of suppleness and feel by comparing the above antibody-treated tufts with tufts which were not antibody-treated. The number of people who decided on each description of the results are shown.

As comparative examples, hair treated with PBS, a control antibody PBS solution or collagen hydrolysate were employed. The results are shown in Table 11.

TABLE 11

| Treating conditions | Suppleness | | | Feel | | |
| --- | --- | --- | --- | --- | --- | --- |
| | Good | Un-changed | Poor | Good | Un-changed | Poor |
| Antibody E-2 | 8 | 2 | 0 | 7 | 2 | 1 |
| Control antibody | 1 | 8 | 1 | 0 | 9 | 1 |
| Collagen hydrolysate | 2 | 7 | 1 | 1 | 8 | 1 |
| PBS (control) | 1 | 9 | 0 | 0 | 8 | 2 |

As is apparent from Tables 9, 10 and 11, significant results were obtained in that the anti-hair keratin antibody according to the present invention was excellent in effects on modification of both luster and combability and could impart a supple, good feel to the hair. In contrast therewith, the ordinary antibody having no specificity or the collagen hydrolysate exhibited no effect on hair modification.

EXAMPLE 1

Shampoo

A shampoo was prepared by blending the underlisted ingredients according to a conventional process.

| Ingredient | Weight % |
| --- | --- |
| Sodium sulfate of polyoxyethylene lauryl ether (2 E.O.) | 15.0 |
| Coconut oil fatty acid diethanolamide | 5.0 |
| Ethyleneglycol distearate | 1.5 |
| Sodium benzoate | 0.2 |
| EDTA | 0.2 |
| Sodium chloride | 1.0 |
| Pigment | proper |
| Perfume | proper |
| Antibody A | 1.0 |
| Refined water | balance |

The hair which was washed with the above shampoo of Example 1 gained a good finish with respect to combability, smoothness, luster, feel, etc., without brittleness, as compared with a shampoo of the same composition as Example 1 except that Antibody A was not used.

EXAMPLE 2

Hair Rinse

A hair rinse was prepared by blending the underlisted ingredients according to a conventional process.

| Ingredient | Weight % |
| --- | --- |
| Stearyltrimethylammonium chloride | 3.0 |
| Cetanol | 2.0 |
| Glycerin monostearate | 1.5 |
| 1,3-Butylene glycol | 5.0 |
| Liquid paraffin | 2.0 |
| Collagen hydrolysate | 0.5 |
| Pigment | proper |
| Perfume | proper |
| Antibody A | 0.5 |
| Refined water | balance |

The hair treated with the above hair rinse of Example 2 after washing with a commercially available shampoo was preferred with respects of dampness, luster, combability, etc., as compared with that treated with a hair rinse of the same composition as Example 2 except that Antibody A was not used.

EXAMPLE 3

Hair Treatment

A hair treatment was prepared by blending the under-listed ingredients according to a conventional process.

| Ingredient | Weight % |
| --- | --- |
| Stearyltrimethylammonium chloride | 3.0 |
| Cetanol | 2.0 |
| Glycerin monostearate | 1.5 |
| 1,3-Butylene glycol | 5.0 |
| Liquid paraffin | 2.0 |
| Collagen hydrolysate | 0.5 |
| Pigment | proper |
| Perfume | proper |
| Antibody A | 0.5 |
| Refined water | balance |

The hair treated with the above hair treatment of Example 3, after washing with a commercially available shampoo, gained good combability, dampishness and luster, as compared with that treated with a hair treatment having the same composition as Example 3 except that Antibody A was not used. Particularly, this hair treatment showed a good effect in repairing damaged hair.

EXAMPLE 4

Hair Cream

A hair cream was prepared by blending the underlisted ingredients according to a conventional process.

| Ingredient | Weight % |
| --- | --- |
| Stearic acid | 5.0 |
| Stearylalcohol | 2.0 |
| Sorbitan monostearate (20 E.O.) | 3.0 |
| Liquid paraffin | 15.0 |
| Beeswax | 2.0 |
| Lanolin | 2.0 |
| Glycerin | 3.0 |
| Polyvinylalcohol | 1.0 |
| Antiseptic | proper |
| Perfume | proper |
| Antibody B | 1.0 |
| Refined water | balance |

The hair treated with the above hair cream of Example 4 was excellent used dampness, luster, suppleness and smoothness, as compared with that treated with a hair cream having the same composition as Example 4 except that Antibody B was not used. Moreover, damage to the hair such as brittleness was repaired.

EXAMPLE 5

Hair Tonic

A hair tonic was prepared by blending the underlisted ingredients according to a conventional process.

| Ingredient | Weight % |
| --- | --- |
| Biosol | 0.1 |
| Salicylic acid | 0.2 |
| L-menthol | 0.2 |
| Capronium chloride | 0.5 |
| Inositol | 0.1 |
| Ethanol | 20.0 |
| Perfume | proper |
| Antibody C | 1.0 |
| Refined water | balance |

The hair treated with the above hair tonic of Example 5 was excellent with respect to dampness, luster and mild feel as compared with that treated with a hair tonic having the same composition as Example 5 except that Antibody C was not used.

EXAMPLE 6

Hair Lotion

A hair lotion was prepared by blending the underlisted ingredients according to a conventional process.

| Ingredient | Weight % |
| --- | --- |
| Ethanol | 10.0 |
| Polyoxyethylene sorbitan monooleate (20 E.O.) | 1.0 |
| Antiseptic | proper |
| Perfume | proper |
| Antiserum A | 0.5 |
| Refined water | balance |

The hair treated with the above hair lotion of Example 6 and dried with a dryer gained good dampness and tautness as well as preferable smoothness and suppleness as compared with that treated with a hair lotion having the same composition as Example 6 except that Antiserum A was not used.

EXAMPLE 7

Treatment Foam

A treatment foam was prepared by charging a spray can with 95 parts of a substrate liquid obtained by blending the under-listed ingredients according to a conventional process and 5 parts of liquefied petroleum gas (LPG) admixed therewith as a propellant.

| Ingredient | Weight % |
| --- | --- |
| Stearyltrimethylammonium chloride | 0.4 |
| Liquid paraffin | 1.0 |
| Silicone oil | 2.0 |
| Propylene glycol | 3.0 |
| Castor oil hardened with polyoxyethylene (80 E.O.) | 1.0 |
| Castor oil hardened with polyoxyethylene (10 E.O.) | 0.5 |
| Sodium citrate | 0.2 |
| Ethanol | 7.0 |
| Perfume | proper |
| Antiserum B | 0.5 |
| Refined water | balance |

| Ingredient | Weight % |
| --- | --- |
| Ammonium thioglycolate (50%) | 12.0 |
| Monoethanolamine | 1.0 |
| Ammonia water | 1.0 |
| Collagen hydrolysate solution | 5.0 |
| EDTA | 0.05 |
| Perfume | proper |
| Antibody A | 1.0 |
| Antibody B | 1.0 |
| Refined water | balance |

The hair treated with the above treatment foam of Example 7 gained good dampness and tautness as well as preferable smoothness and suppleness as compared with that treated with a treatment foam having the same composition as Example 7 except that Antiserum B was not used. Particularly, this treatment foam showed an effect of repairing or modifying damaged hair.

EXAMPLE 8

Brushing Spray

A brushing spray was prepared by charging a spray can with 30 parts of a substrate liquid obtained by blending the under-listed ingredients according to a conventional process and 70 parts of liquefied petroleum gas (LPG) admixed therewith as a propellant.

| Ingredient | Weight % |
| --- | --- |
| Behenyltrimethylammonium chloride | 0.1 |
| Liquid paraffin | 3.0 |
| Silicone oil | 3.0 |
| Ethanol | 7.0 |
| Perfume | proper |
| Antiserum C | 0.5 |
| Ethanol | 10.0 |
| Refined water | balance |

The hair treated with the above brushing spray of Example 8 and brushed repeatedly showed less damage and splitting of the hair as compared with that treated with a brushing spray having the same composition as Example 8 except that Antiserum C was not used. Further, its luster, combability and suppleness were also good.

EXAMPLE 9

Primary Reagent for Perming

A primary reagent for perming was prepared by blending the under-listed ingredients according to a conventional process.

| Ingredient | Weight % |
| --- | --- |
| Paraphenylene diamine | 0.3 |
| Resorcin | 0.2 |
| Metaaminophenol | 0.03 |
| Paraaminophenol | 0.05 |
| Ammonia water | 7.5 |
| Cetanol | 16.0 |
| Sodium laurylsulfate | 4.2 |
| Sodium sulfite | 0.2 |
| Hydrolyzed gelatin | 3.0 |
| EDTA | proper |
| Perfume | proper |
| Antibody A | 1.0 |
| Antiserum C | 1.0 |
| Refined water | balance |

The hair treated with the above perming primary reagent of Example 9 and further treated with a commercially available secondary reagent showed less damage to the hair, good settability and set retention, and was given an excellent finish with respect to luster, suppleness or the like.

EXAMPLE 10

Primary Reagent for Hair Color

A primary reagent for a hair color was prepared by blending the under-listed ingredients according to a conventional process.

| Ingredient | Weight % |
| --- | --- |
| Paraphenylene diamine | 0.3 |
| Resorcin | 0.2 |
| Metaaminophenol | 0.03 |
| Paraaminophenol | 0.05 |
| Ammonia water | 7.5 |
| Cetanol | 16.0 |
| Sodium laurylsulfate | 4.2 |
| Sodium sulfite | 0.2 |
| Hydrolyzed gelatin | 3.0 |
| EDTA | proper |
| Perfume | proper |
| Antibody A | 1.0 |
| Antiserum C | 1.0 |
| Refined water | balance |

The above hair color primary reagent of Example was admixed with a 6% hydrogen peroxide aqueous solution at a ratio of 1:1 and a hair color treatment was conducted according to a conventional process. The treated hair showed less damage and was given an excellent finish with respect to luster, suppleness or the like.

EXAMPLE 11

Shampoo

A shampoo was prepared with the purified antibody obtained in Manufacturing Example 3. The blended composition was as follows:

| Ingredient | Weight % |
| --- | --- |
| Sodium sulfate of polyoxyethylene laurylether (2 E.O.) | 15.0 |
| Coconut oil fatty acid diethanolamide | 5.0 |
| Ethylene glycol distearate | 1.5 |
| Sodium benzoate | 0.2 |
| EDTA | 0.2 |
| Pigment | proper |
| Perfume | proper |
| Antibody E-2 | 1.0 |
| Refined water | balance |

The above shampoo of Example 11 provided the hair with a good finish with respect to combability, smoothness, luster, feel, etc., without brittleness, as compared with a shampoo of the same composition as Example 11 except that the antibody was not compounded.

EXAMPLE 12

Hair Treatment

A hair treatment was prepared with the high purity refined antibody obtained in Manufacturing Example 3 (Antibody E-3). The blended composition was as follows:

| Ingredient | Weight % |
| --- | --- |
| Distearyldimethylammonium chloride | 1.0 |
| Cetanol | 5.0 |
| Glycerin monostearate | 2.0 |
| Propylene glycol | 6.0 |
| Pigment | proper |
| Perfume | proper |
| Antibody E-3 | 0.1 |
| Refined water | balance |

The hair treated with the above hair treatment of Example 12 after washing with a commercially available shampoo was given good combability, dampness and luster, as compared with that treated with a hair treatment having the same composition as Example 12 except that the antibody was not compounded. Particularly, this hair treatment exhibited a good effect in repairing damage to the hair Further, it gave the hair a good finish with respect to feel or the like.

INDUSTRIAL APPLICABILITY

The present invention provides hair modifiers or hair damage protectives which do not bind to the skin but bind specifically to the hair by virtue of a strong avidity, thereby having capabilities of preventing elusion of proteins from the hair, improving combability, effectively modifying luster, suppleness, feel or the like of the hair, and preventing and repairing damage to the hair.

Further, the present invention has provided hair care products which bind specifically to the hair by virtue of a strong avidity, thereby having capabilities of preventing elusion of constituent proteins from the hair, improving combability, effectively modifying luster, suppleness, feel or the like of the hair, and preventing and repairing damage to the hair.

Furthermore, the present invention has provided an effective process for producing an anti-hair keratin antibody useful as hair modifiers which do not bind to the skin but bind specifically to the hair by virtue of a strong avidity, thereby having capabilities of preventing elusion of constituent proteins from the hair, improving combability, effectively modifying luster, suppleness, feel or the like of the hair, and preventing and repairing damage to the hair.

We claim:

1. A hair treatment composition which comprises, as an active ingredient, an antibody which binds to cornified human hair keratins which constitute intermediate filaments found in the cortex portion and a carrier.

2. The hair treatment composition of claim is therein said antibody is obtained by immunizing an animal with human hair keratins which constitute filaments.

3. A process for producing an antibody which binds to human hair keratins which constitute intermediate filaments from a bovid animal, which process comprises immunizing said bovid animal with human hair keratins which constitute intermediate filaments found in the cortex portion as an antigen and recovering said antibody from the milk of said bovid animal.

4. The process according to claim 3, wherein said bovid animal is a cow.

* * * * *